(12) United States Patent
Peng et al.

(10) Patent No.: US 10,175,435 B2
(45) Date of Patent: Jan. 8, 2019

(54) MEDICAL LASER DEVICE AND RELATED METHODS

(71) Applicant: Boston Scientific Scimed, Inc., Maple Grove, MN (US)

(72) Inventors: Steven Yihlih Peng, Fremont, CA (US); Wen-Jui Ray Chia, Sunnyvale, CA (US); Thomas Charles Hasenberg, Campbell, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 15/729,718

(22) Filed: Oct. 11, 2017

(65) Prior Publication Data

US 2018/0098811 A1 Apr. 12, 2018

Related U.S. Application Data

(60) Provisional application No. 62/406,706, filed on Oct. 11, 2016, provisional application No. 62/445,770, filed on Jan. 13, 2017.

(51) Int. Cl.
*G02B 6/42* (2006.01)
*G02B 6/02* (2006.01)
(Continued)

(52) U.S. Cl.
CPC .......... *G02B 6/4296* (2013.01); *A61B 18/201* (2013.01); *A61B 18/22* (2013.01); *A61B 18/26* (2013.01); *G02B 6/02* (2013.01); *G02B 6/02066* (2013.01); *G02B 6/02147* (2013.01); *G02B 6/02342* (2013.01); *G02B 6/4292* (2013.01);
(Continued)

(58) Field of Classification Search
CPC .... G02B 6/4296; G02B 6/02; G02B 6/02066; G02B 6/02147; G02B 6/02342; G02B 6/443; G02B 6/4292; A61B 18/26; A61B 18/22; A61B 18/201
See application file for complete search history.

(56) References Cited

U.S. PATENT DOCUMENTS

| | | | |
|---|---|---|---|
| 6,282,349 B1 | 8/2001 | Griffin | |
| 6,953,288 B2 * | 10/2005 | Foley | .................. G02B 6/4292 385/60 |
| 9,122,009 B1 * | 9/2015 | Griffin | ..................... C03B 37/15 |
| 2014/0211818 A1 | 7/2014 | Hou et al. | |

FOREIGN PATENT DOCUMENTS

| | | |
|---|---|---|
| CN | 204992235 U | 1/2016 |
| EP | 1544649 A1 | 6/2005 |

OTHER PUBLICATIONS

Etsion ("State of the Art in Laser Surface Texturing", Journal of Tribology, Jan. 2005, 127, 248-253).*

(Continued)

*Primary Examiner* — Ryan A Lepisto
(74) *Attorney, Agent, or Firm* — Bookoff McAndrews, PLLC

(57) ABSTRACT

A laser delivery device may include a connector portion at a proximal end of the laser delivery device and an optical fiber connecting the connector portion to a distal end of the laser delivery device. The connector portion may include a capillary at least partially surrounding a proximal portion of the optical fiber, and the capillary may include dimples on at least a portion of a circumferential surface thereof.

20 Claims, 7 Drawing Sheets

(51) Int. Cl.
*A61B 18/26* (2006.01)
*G02B 6/44* (2006.01)
*A61B 18/22* (2006.01)
*A61B 18/20* (2006.01)
*H01S 3/16* (2006.01)
*A61B 18/00* (2006.01)
*A61N 5/067* (2006.01)

(52) U.S. Cl.
CPC .... *G02B 6/443* (2013.01); *A61B 2018/00505* (2013.01); *A61B 2018/2266* (2013.01); *A61N 2005/067* (2013.01); *G02B 2006/4297* (2013.01); *H01S 3/161* (2013.01); *H01S 3/1643* (2013.01)

(56) References Cited

OTHER PUBLICATIONS

International Search Report and Written Opinion for corresponding International Application No. PCT/US2017/056028, dated Dec. 21, 2017 (10 pages).
Etsion, I. State of the Art in Laser Surface Texturing J. of Tribology, Jan. 2005, 127, 248-253.†
ThorLabs, SMA 905 Multimode Connectors, Jun. 7, 2012. [Retrieved on Apr. 26, 2018] Retrieved from the Internet URL https//web.archive.org/web/20120607215646/ https//www.thorlabs.com/newgrouppage9.cfm? objectgroup_id=1383.†

\* cited by examiner
† cited by third party

MEDICAL LASER DEVICE AND RELATED METHODS

CROSS-REFERENCE TO RELATED APPLICATIONS

This application claims the benefit of priority of U.S. Provisional Application Nos. 62/406,706, filed Oct. 11, 2016, and 62/445,770, filed Jan. 13, 2017, the entireties of which are incorporated by reference into this application.

TECHNICAL FIELD

Various aspects of the present disclosure relate generally to medical laser devices and related methods. More specifically, the present disclosure relates to medical laser devices and connectors for transmitting select modes of laser energy through a fiber.

BACKGROUND

Lasers have been used in, for example, urology, neurology, otorhinolaryngology, general anesthetic ophthalmology, dentistry, gastroenterology, cardiology, gynecology, thoracic, and orthopedic procedures. One example of a procedure that may be performed using a laser is lithotripsy. Lithotripsy involves treating a subject's kidneys, ureters, or bladder by removing material therein, such as calculi or stones. Laser lithotripsy is a subset of lithotripsy where laser energy is applied to break down targeted material, thereby facilitating removal of the material. In one exemplary laser lithotripsy procedure, an optical fiber may be inserted through a working channel of an insertion device, such as an endoscope or a ureteroscope, and adjacent to the targeted material. The optical fiber may transmit laser energy to the targeted material to break down the targeted material into pieces. The pieces may then be washed out of, or otherwise removed from, the subject.

However, often in laser lithotripsy, the size of the optical fiber in the laser delivery device limits the power of the laser that can be delivered to the targeted material, thus limiting the ability to break down the material. A powerful laser emits higher order laser energy that may escape an optical fiber and be absorbed by components in a handle of the laser delivery device, heating those components to unsafe temperatures and posing a risk to a user. A powerful laser may also overheat the optical fiber, which may break the optical fiber or burn a subject.

The devices and methods of the current disclosure may rectify some of the deficiencies described above, or address other aspects of the prior art.

SUMMARY

Examples of the present disclosure relate to, among other things, medical laser devices. Each of the examples disclosed herein may include one or more of the features described in connection with any of the other disclosed examples.

In one example, a laser delivery device may include a connector portion at a proximal end of the laser delivery device, and an optical fiber connecting the connector portion to a distal end of the laser delivery device. The connector portion may including a capillary at least partially surrounding a proximal portion of the optical fiber, wherein the capillary includes dimples on at least a portion of a circumferential surface thereof.

The laser delivery device may further include one or more of the following features. The dimples may be included on an outer circumferential surface thereof. The dimples may be arranged in a pattern. The dimples may be arranged randomly. The capillary may be glass. The dimples may be a constant depth, or the dimples may be varying depths. The dimples may be formed by melting with a $CO_2$ laser. The dimples may be not included on a distal outer circumferential surface portion of the capillary. An outer circumferential surface of the capillary also includes projections. The optical fiber may include a core surrounded by at least one cladding layer and/or one buffer layer; and the optical fiber may be at least partially surrounded by a jacket layer. The capillary may include a dimple free portion at a proximal end of the capillary and may be fused to the optical fiber at proximal ends of the capillary and the optical fiber. At least a portion of the capillary may be radially surrounded by a stainless steel ferrule. A portion of the capillary may be surrounded by a crimp, and the optical fiber may pass through the crimp. The laser delivery device may be coupled to a holmium laser.

In another example, a laser delivery device may include an SMA connector. The SMA connector may include a capillary at least partially surrounding a portion of an optical fiber, and the capillary may include dimples on at least a portion of a circumferential surface thereof.

The laser delivery device may further include one or more of the following features. The optical fiber may be fused to the capillary at least over a portion of the optical fiber. The dimples may be included on an outer circumferential surface of the capillary.

In another example, a laser delivery device may include a connector portion at a proximal end of the laser delivery device, and an optical fiber connecting the connector portion to a distal end of the laser delivery device. The connector portion may include a capillary at least partially surrounding a proximal portion of the optical fiber, and the capillary may include a dimple free portion at a proximal most end and a dimpled portion.

The laser delivery device may further include one or more of the following features. The capillary may be fused to the optical fiber over the overlap of the dimple free portion with the optical fiber. The dimpled portion may include dimples on an outer circumferential surface of the capillary. The dimples on the dimpled portion of the outer circumferential surface of the capillary may be formed by melting with a $CO_2$ laser.

Both the foregoing general description and the following detailed description are exemplary and explanatory only and are not restrictive of the features, as claimed. As used herein, the terms "comprises," "comprising," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal." As used herein, the terms "about," "substantially," and "approximately," indicate a range of values within +/−5% of a stated value.

BRIEF DESCRIPTION OF THE DRAWINGS

The accompanying drawings, which are incorporated in and constitute a part of this specification, illustrate exemplary features of the present disclosure and together with the description, serve to explain the principles of the disclosure.

DETAILED DESCRIPTION

Examples of the present disclosure relate to medical devices for delivering laser energy to target tissue or material. The medical device may be delivered through any appropriate insertion device or alone through a bodily orifice.

Reference will now be made in detail to examples of the present disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary medical device or insertion device. When used herein, "proximal" refers to a position relatively closer to the exterior of the body or closer to an operator using the medical device or insertion device. In contrast, "distal" refers to a position relatively further away from the operator using the medical device or insertion device, or closer to the interior of the body.

Figure 1:
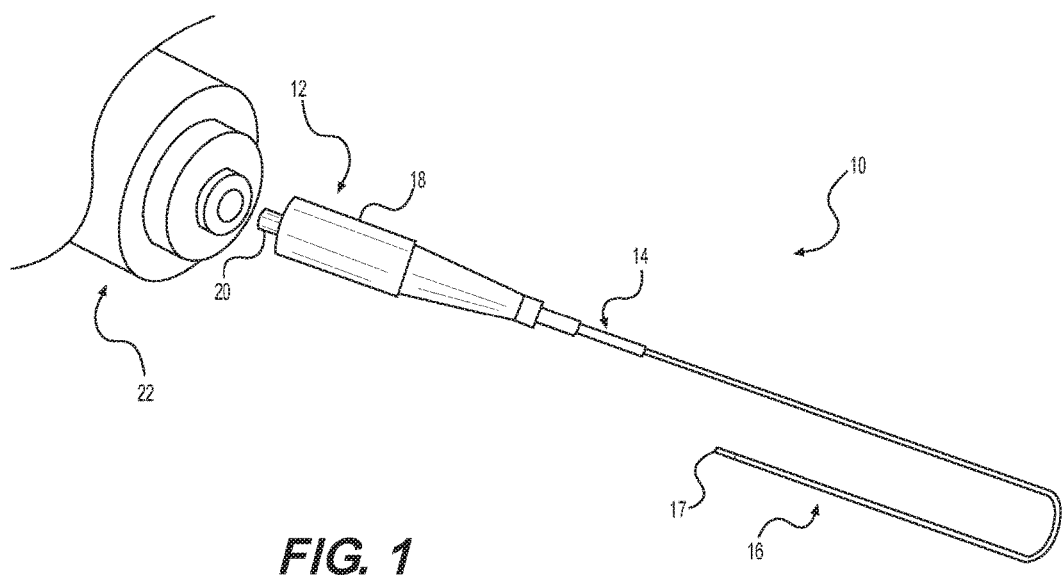
FIG. 1 illustrates an exemplary medical laser delivery device.

FIG. 1 illustrates a laser delivery device 10 with a proximal portion 12, an intermediate portion 14, and a distal portion 16 with a distal tip 17. Proximal portion 12 may include a handle 18 having a connector portion 20. Laser delivery device 10 may couple to a laser source 22 via connector portion 20 and transmit energy through an internal fiber in laser delivery device 10 and out of distal tip 17 to targeted material.

Figure 2:
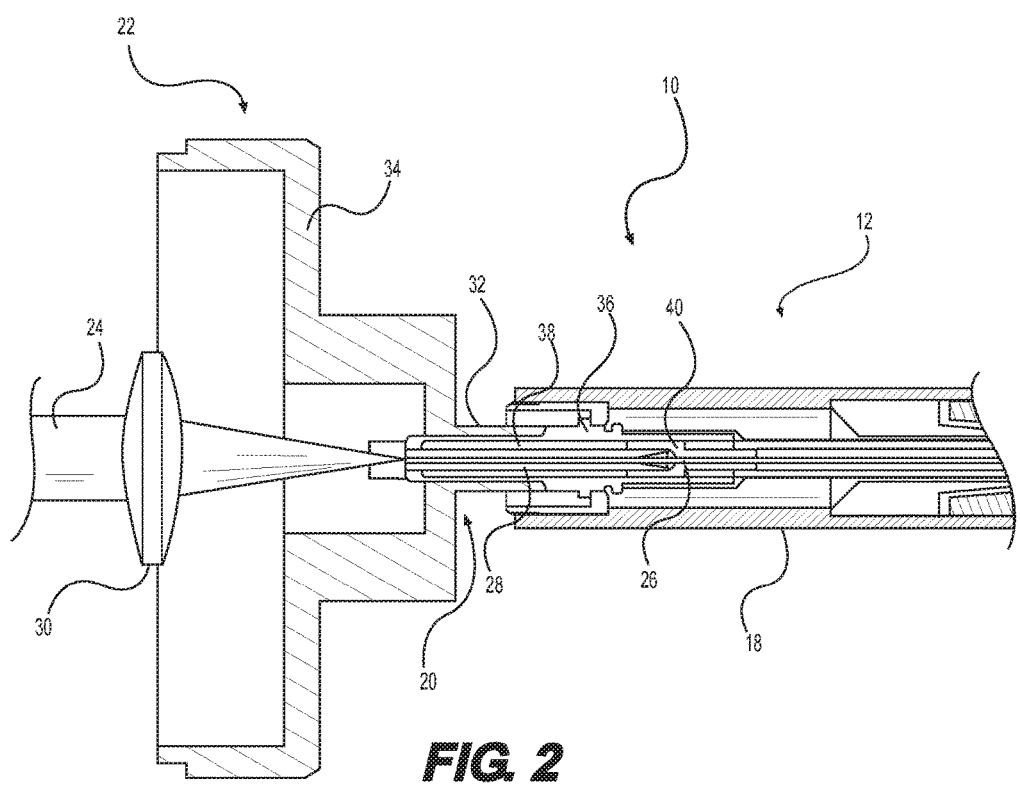
FIG. 2 illustrates a cross-section of a portion of the medical laser delivery device of FIG. 1 coupled to a laser source.

FIG. 2 illustrates proximal portion 12 of laser delivery device 10 with connector portion 20 mated to laser source 22. Laser delivery device 10 may receive laser energy 24 from the laser source 22 to be delivered through an optical fiber 26 that extends through the laser delivery device 10 to the distal tip 17 at distal portion 16. A portion of optical fiber 26 within connector portion 20 may be at least partially surrounded by a capillary 28, which as will be discussed in more detail below may be dimpled to scatter incident light.

Laser source 22 may include a lens 30 to narrow the laser energy 24, and may also include a port 32 extending from laser housing 34 to receive and mate with connector portion 20 of laser delivery device 10 in order to transmit laser energy 24 through laser delivery device 10. Laser source 22 may be, for example, a holmium YAG (Ho:YAG) laser source emitting laser energy 24 with a wavelength of approximately 2.1 µm and a power of approximately 100 W. Laser source 22 may generate laser energy 24 with a shallow penetration depth of approximately 0.4 mm. In other aspects, laser source 22 may be a Thulium-doped YAG (Tm:YAG) laser source, a Thulium Fiber laser source, a neodymium-doped YAG (Nd:YAG) laser source, a semiconductor laser diode, an Erbium-doped YAG (ER:YAG) laser source, or a frequency doubled Nd:YAG laser source utilizing either a potassium-titanyl phosphate crystal (KTP), or a Lithium Borate crystal (LBO) as the doubling crystal. Though not shown, laser source 22 may have a control module to control a timing, a wavelength, and/or a power of the laser energy 24. The control module may control laser selection, filtering, temperature compensation, and/or Q-switching.

As noted above, laser delivery device 10 may mate with laser source 22 through connector portion 20. Connector portion 20 may include optical fiber 26 and capillary or tube 28 radially surrounding a proximal portion of the optical fiber 26. Connector portion 20 may further include a ferrule 36 radially surrounding at least a portion of optical fiber 26 and capillary 28. There may be a circumferential hollow portion 38 or gap between a portion of ferrule 36 and a portion of capillary 28. Optical fiber 26 may extend through laser delivery device 10 from the connector portion 20 to the distal tip 17 to receive and transmit laser energy 24 from laser source 22 to targeted material. Capillary 28 include a dimpled outer surface to scatter incident laser energy 24 that escapes optical fiber 26. Capillary 28 may be fused to optical fiber 26 at least over a portion of their overlap (FIG. 2), for example at the proximal ends of optical fiber 26 and capillary 28. In one aspect, where optical fiber 26 is fused to capillary 28, optical fiber 26 only includes a fiber core and is not enclosed by buffer layers or jacket layers. Fiber core of optical fiber 26 may be fused to capillary 28 at the proximal ends of optical fiber 26 and capillary 28. Alternatively, fiber core of optical fiber 26 may be fused to capillary 28 for over the length of the capillary 28 that radially surrounds optical fiber 26. More distal portions of optical fiber 26 may be enclosed by various other layers. Ferrule 36 may include radial projections such that it may be coupled to handle 18.

Connector portion 20, along with ferrule 36 and the enclosed components, may be any type of SubMiniature version A ("SMA") connector or another appropriate optical fiber connector to mate with port 32. Connector portion 20 may include a central fiber to receive and transmit laser energy 24 from laser source 22, and may also include an outer threading in order to be coupled to port 32. For example, connector portion 20 may be a male SMA connector if port 32 is a female SMA connector, or connector portion 20 may be a female SMA connector if port 32 is a male SMA connector. Ferrule 36 may be stainless steel or another appropriate material. A crimp 40 may also radially surround a portion of optical fiber 26 and a portion of capillary 28. Crimp 40 may have a cup-like shape in a proximal portion where it surrounds both optical fiber 26 and capillary 28, and may extend longitudinally in a distal direction surrounding the optical fiber 26. Crimp 40 may be brass, aluminum, or another appropriate material. Capillary 28, ferrule 36, and crimp 40 may be coupled via glue, epoxy, or another appropriate adhesive.

Figure 3:
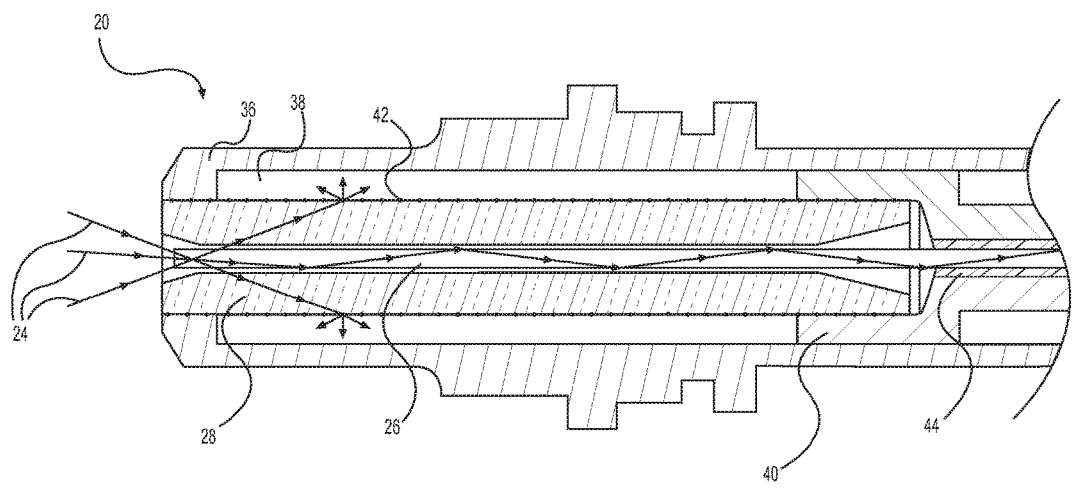
FIG. 3 illustrates a cross-section of a portion of the medical laser delivery device of FIG. 1.

As shown in FIG. 3, capillary 28 may surround optical fiber 26 and may be proximally flush with a proximal end of ferrule 36. Optical fiber 26 may be slightly recessed within capillary 28. Optical fiber 26 may pass through a longitudinal core of laser delivery device 10, as shown in FIGS. 1 and 2. Optical fiber 26 may extend the length of laser delivery device 10 to receive laser energy 24 at the junction of connector portion 20 with laser source 22 and to deliver laser energy 24 to the targeted material from distal tip 17 at the distal portion 16 of laser delivery device 10.

Optical fiber 26 may have a circular cross-section and may comprise a fiber core surrounded by one or more cladding layers (not shown), which may also be surrounded by one or more buffer layers (not shown). Distally beyond capillary 28, optical fiber 26 may be surrounded by one or more jacket layers 44 through crimp 40 and to distal portion 16 of laser delivery device 10. Jacket layers 44 may be bonded to crimp 40 through an adhesive or may be joined by crimp 40 pinching jacket layers 44 around optical fiber 26. Optical fiber 26 may be a silica-based optical fiber. The core of optical fiber 26 may be made of a suitable material to transmit laser energy 24, such as, for example, silica with low hydroxyl ($OH^-$) ion residual concentration. Like the core of the optical fiber 24, the one or more cladding layers may be pure silica or doped silica with, for example, fluorine. The one or more cladding layers may be a single or double cladding, and may be made of a hard polymer or silica. The one or more buffer layers may be an acrylate layer or may be made of a hard polymer, such as, for example, Tefzel®.

The distal tip 17 of laser delivery device 10 may be a spherical end, a straight-firing end, a side-firing end, or another appropriate end. The distal tip 17 of laser delivery device 10 emits the laser energy 24 toward the targeted material, so optical fiber 26 serves as a waveguide for laser energy 24.

Figure 4:
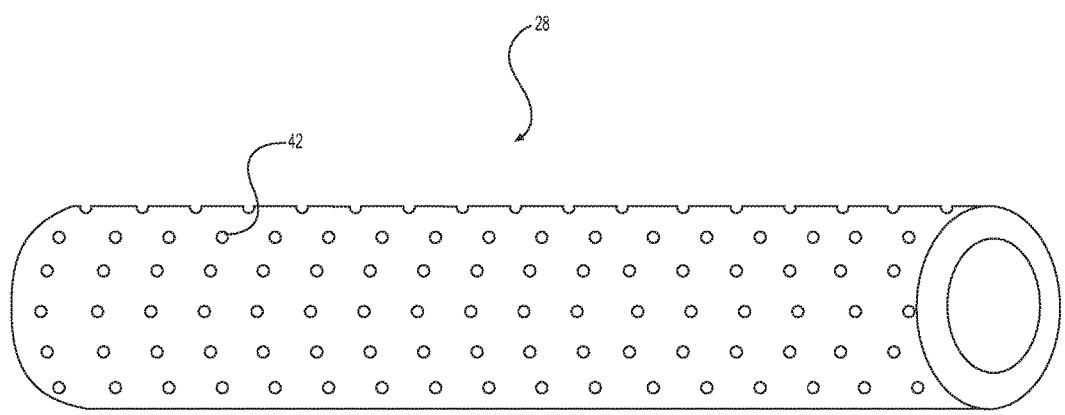
FIG. 4 illustrates a perspective view of a dimpled capillary of the exemplary medical laser delivery device.

As shown in FIG. 4, capillary 28 may be a hollow tube with dimples 42. Capillary 28 radially surrounds optical fiber 26 within connector portion 20 and is partially surrounded by crimp 40 (FIGS. 2 and 3). The hollow portion or lumen within capillary 28 may widen at the proximal end and distal end of capillary 28. Capillary 28 may be formed of glass, silica, sapphire, or another appropriate material.

The dimples 42 may be located on the outer circumferential surface of capillary 28 to scatter overfilled laser energy 24 or higher order mode laser energy 24 that escapes from optical fiber 26 toward ferrule 36, as shown in the lines of laser energy 24 in FIG. 3. The dimples 42 on capillary 28 may have equal sizes and depths and be evenly spaced around the entire outer radial surface and length of capillary 28 (FIG. 4). In an alternative aspect, dimples 42 may only be distributed over a portion of the outer radial surface of capillary 28, namely only over that portion of capillary 28 that is exposed to hollow portion 38 (FIG. 3). In another aspect, dimples 42 may be distributed over even less of the circumferential surface of the capillary 28. Dimples 42 may also be distributed over all or a portion of both the inner and outer circumferential surfaces of the capillary 28.

Dimples 42 may be depressions, indentations, hollows, bubbles, notches, frostings, or perforations. Dimples 42 may be spherical, elliptical, or another shape. Dimples 42 may partially extend through the radial thickness of capillary 28, and may be constant or varying depths. In one aspect, dimples 42 may extend between 1 and 50 micrometers through the radial thickness of capillary 28. Alternatively, outer and/or inner circumferential surface of capillary 28 may include bumps (not shown), or a combination of dimples 42 and bumps. Moreover, dimples 42 or bumps may be arranged in capillary 28 in a pattern (as shown) or randomly positioned, and may be evenly spaced or unevenly spaced. Furthermore, capillary 28 may include a plurality of internally dispersed particles to scatter the higher order mode or overfilled portions of laser energy 24.

Dimples 42 may be formed in or on capillary 28 by melting specific spots with a $CO_2$ laser or a green light laser. Dimples 42 may be formed in or on capillary 28 through a mechanical or chemical etching process. Dimples 42 may be preformed in capillary 28, or may otherwise be formed in capillary 28.

During use, laser delivery device 10 may be inserted in an already positioned insertion device, such as a ureteroscope or an endoscope. Handle 18 may then be connected to laser source 22 via connector portion 20 and port 32 (FIG. 2). Once activated, laser source 22 provides laser energy 24 to laser delivery device 10, with the laser energy 24 propagating through optical fiber 26 to be applied to the targeted material. Higher order mode and overfilled portions of laser energy 24 may escape optical fiber 26 and enter capillary 28 within the first few millimeters of the connector portion 20 from port 32, as shown in FIG. 3.

The higher order mode and overfilled portions of laser energy 24, which heat up components when absorbed, have a tendency to refract and bounce within connector portion 20 and optical fiber 26. However, dimples 42 on the outer radial surface of capillary 28 may assist in scattering some of the higher order mode and overfilled portions of laser energy 24 and thus reduce the amount of stray energy downstream of the capillary 28. An increase in or greater distribution of dimples 42 on capillary 28 may scatter a greater portion of the higher order mode and overfilled portions of laser energy 24 and thus further assist in reducing the detrimental effects downstream of the capillary 28. The scattering of the higher order mode and overfilled portions of laser energy 24 by the dimples 42 of capillary 28 may be absorbed by the proximal portion of ferrule 36, as shown in FIG. 3. However, heating up this portion of the laser delivery device 10 is preferred over allowing this stray or refracted energy to travel downstream of the capillary 28. The ferrule 36 is better suited to absorb scattered portions of laser energy 24 and undergo the accompanying increase in temperature than more distal components of laser delivery device 10. Further, ferrule 36 and its connections may be insulated from other fragile and/or heat-sensitive components in laser delivery device 10 allowing the ferrule 36 to be a better heat sink. Ferrule 36 and its connections may also be insulated from the outer surface of handle 18 and other components that a user may contact during operation, reducing the risk of injury to the user, even when using a high powered laser source 22. Restated, the dimples 42 help to isolate the detrimental effects of the higher order mode and overfilled portions of laser energy 24 to a portion of the laser delivery device 10 that is better suited to handle the higher order mode and overfilled portions of laser energy 24.

Additionally, the reduction in higher order mode and overfilled portions of laser energy 24 downstream of the capillary 28 due to dimples 42 makes it more likely that the laser energy 24 will be internally reflected within optical fiber 26 until it reaches the targeted material, as shown in FIG. 3. Therefore, including dimples 42 on capillary 28 reduces the risk of the optical fiber 26 and connector portion 20 overheating, even with a powerful laser source 22 like a holmium laser and even at susceptible portions of the optical fiber 26 like bends. Reducing the risk of the optical fiber 26 overheating reduces the risk of the optical fiber 26 breaking and/or burning a subject. As such, a more powerful laser source may be used with laser delivery device 10, allowing for quicker and more effective procedures on targeted material.

Figure 5:
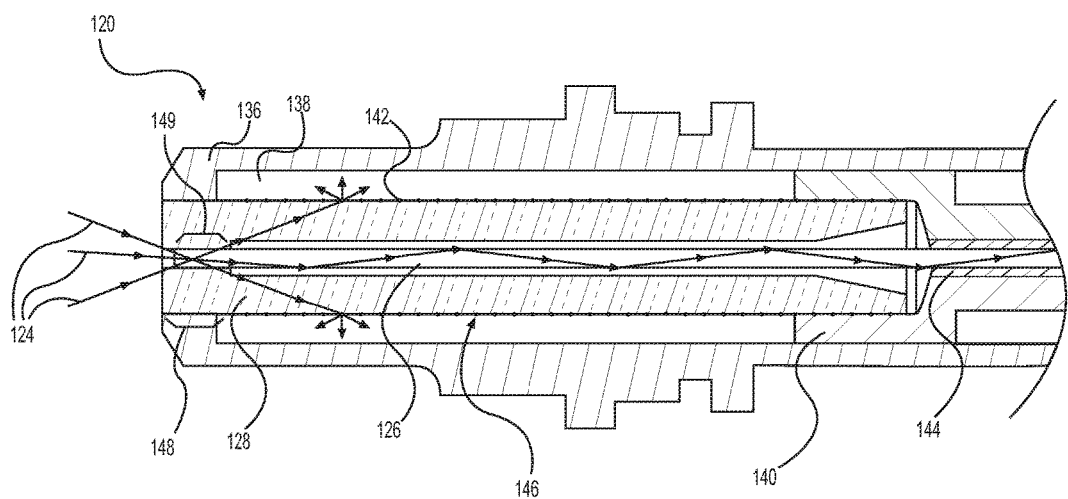
FIG. 5 illustrates a cross-section of a portion of a medical laser delivery device according to another aspect of this disclosure.

As shown in FIG. 5, which is an alternative example with similar elements to the laser delivery device 10 shown by 100 added to the reference numbers, the laser delivery device includes a connector portion 120 that receives laser energy 124. The laser delivery device also includes optical fiber 126, capillary 128, ferrule 136, crimp 140, and jacket layer 144.

In this aspect, capillary 128 includes dimples 142 on a dimpled portion 146, and also includes a dimple free portion 148 at a proximal end of capillary 128. Capillary 128 may surround optical fiber 126, and capillary 128 may be fused to optical fiber 126 over the overlap of the dimple free portion 148 with the optical fiber 126 to form a fused portion 149. Then, connector portion 120 of the laser delivery device may be used to deliver laser energy 124 to target tissue or material. Fused portion 149 ensures that capillary 128 is bonded to optical fiber 126, and the dimples 142 on dimpled portion 146 scatter some of the higher order mode and overfilled portions of laser energy 124.

In one aspect, capillary 128 may have a total length of approximately 20 mm, and dimple free portion 148 may be approximately 2.5 to 5 mm and may extend from the proximal most end of capillary 128. Fused portion 149 may have the same length as dimple free portion 148, or the dimple free portion 148 may extend distal to the fused portion 149. In other aspects, capillary 128 may be longer or shorter, and dimple free portion 148 may be approximately 10-30% of the total length of the capillary 128. Dimpled portion 146 may make up the remaining portion of capillary 128, or may be less than all of the remaining portion of capillary 128. For example dimples 142 may terminate prior to the distal most end of the capillary 128.

Dimples 142 may be depressions, indentations, hollows, bubbles, notches, frostings, or perforations. Dimples 142 may be formed in or on a dimpled portion 146 of capillary 128 by laser etching, such as, for example, by melting specific spots with a $CO_2$ laser or a green light laser. Dimples 142 may alternatively be formed in or on dimpled portion 146 of capillary 128 by mechanical etching, such as, for example, sand blasting. Dimples 142 may also be formed in or on dimpled portion 146 of capillary 128 by chemical etching, such as, for example, with a hydrofluoric acid solution.

Figure 6:
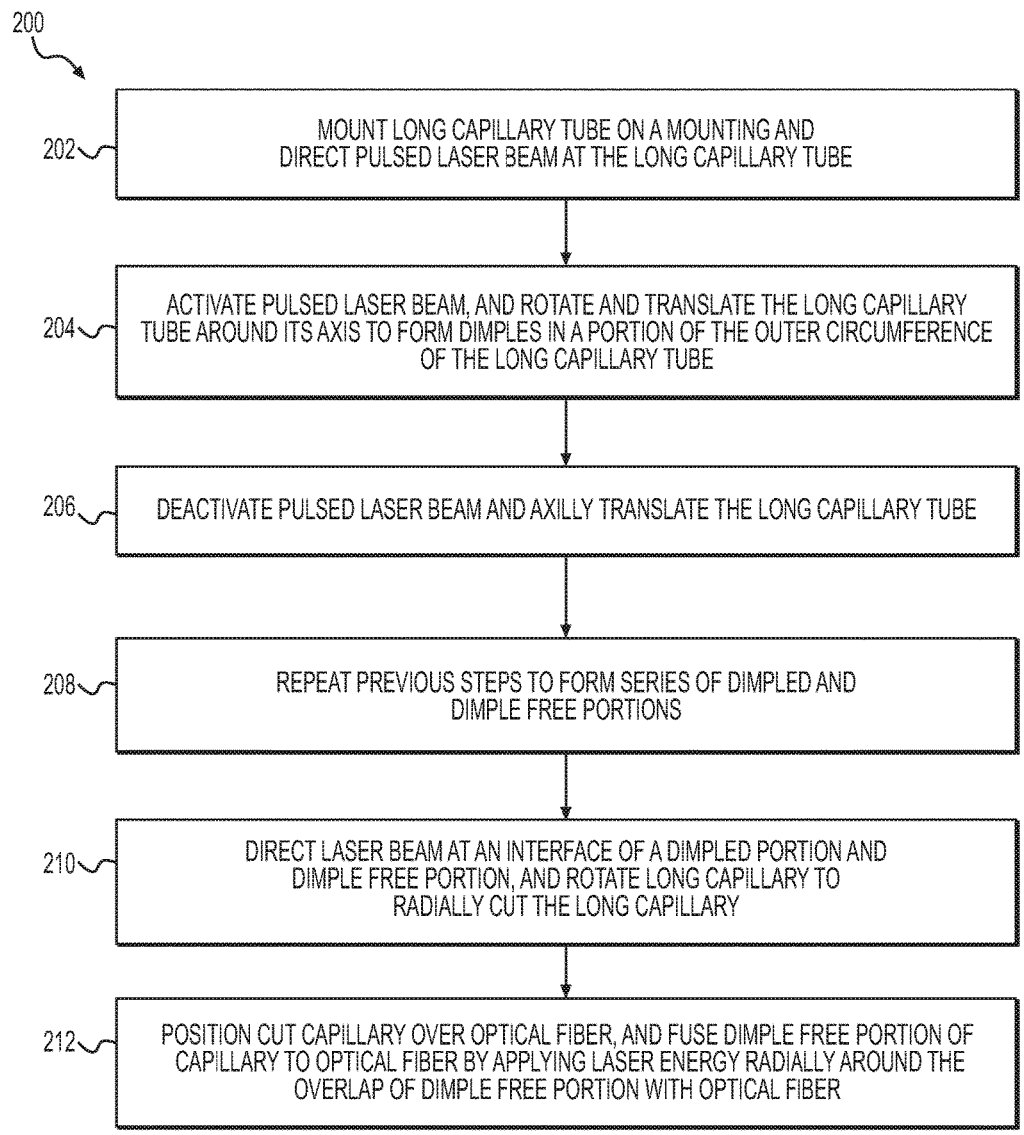
FIG. 6 illustrates a schematic view of an exemplary method of forming a dimpled capillary of the medical laser delivery device of FIG. 5.
Figure 7:
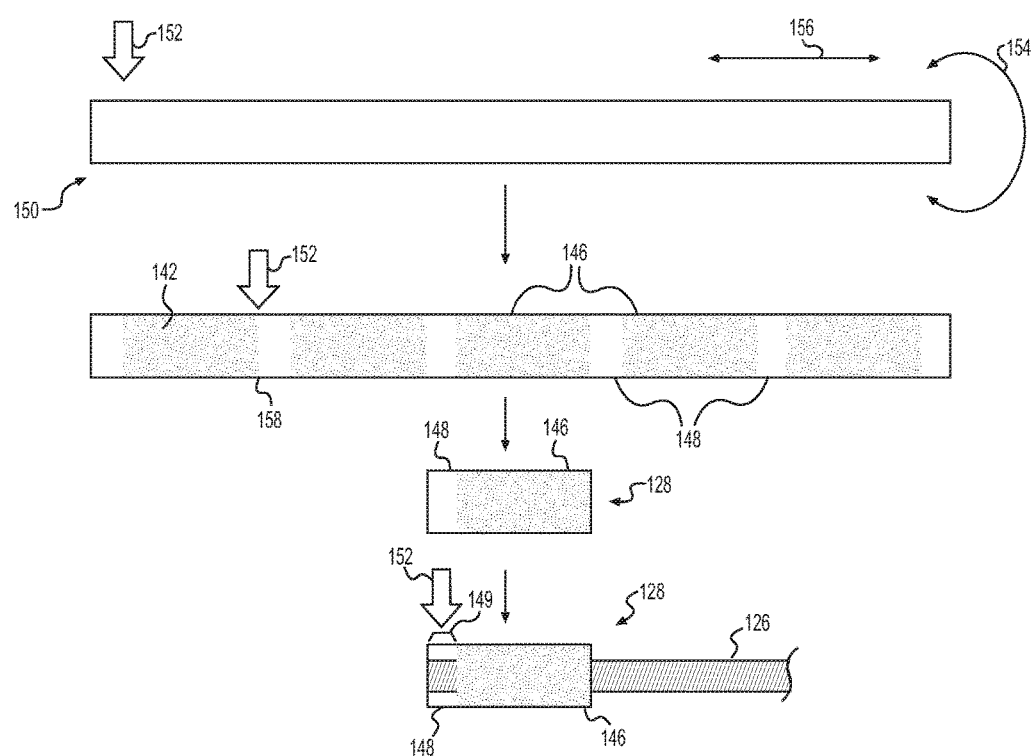
FIG. 7 illustrates a perspective view of the dimpled capillary during the method of FIG. 6.

FIGS. 6 and 7 provide an exemplary method of making capillary 128. For example, a plurality of capillaries 128 with dimples 142 may be formed and fused to optical fibers 126 according to method 200. In step 202, a long capillary tube 150 may be attached on a mounting (not shown), and laser beam 152 may be directed at the capillary tube 150. Laser beam 152 may be a pulsed $CO_2$ laser beam. In step 204, the laser beam 152 may be activated, and the capillary tube 150 may be rotated around its axis in direction 154 by the mounting so as to form dimples 142 in the outer circumference of capillary tube 150. The mounting may also move the capillary tube 150 longitudinally along direction 156 relative to laser beam 152 to dimple the outer circumference of capillary tube 150 to form dimpled portion 146. In step 206, the laser beam 152 may be deactivated or turned off momentarily while the mounting moves capillary tube 150 axially, and then the laser beam 152 may be activated or turned on again. In step 208, the deactivation and reactivation steps may be repeated as the laser beam 152 forms a series of dimpled portions 146 and dimple free portions 148 over the length of capillary tube 150.

Then, in step 210, laser beam 152, which may be adjusted to be a constant laser beam, may be applied to the capillary tube 150 proximate to an interface 158 of one of the dimpled portions 146 and one of the dimple free portions 148. The mounting may halt any axial movement but may rotate in direction 154 to rotate the capillary tube 150 so the laser beam radially cuts capillary tube 150. The laser beam 152 may be applied such that the capillary tube 150 is cut into a plurality of capillaries 128, each having a dimpled portion 146 and a dimple free portion 148. Each capillary 128 may then be used in one laser delivery device 10. Alternatively, the dimpling and cutting steps may be carried out with the capillary tube 150 axially and/or rotationally stationary, and laser beam 152 moving axially and/or rotationally relative to capillary tube 150.

In step 212, capillary 128 may be fused to optical fiber 126. For example, capillary 128 may be positioned over optical fiber 126 such that optical fiber 126 passes through a hollow portion or lumen of capillary 128. Optical fiber 126 may be approximately flush with or slightly distal to the proximal end of capillary 128. Once positioned, capillary 128 may be fused to optical fiber 126 over the overlap of the dimple free portion 148 with the optical fiber 126 to form fused portion 149. Fusion may be accomplished by applying laser energy, which may be the laser beam 152, around the radial circumference of the overlap. As with the dimple formation step, the capillary 128 and optical fiber 126 may be rotated relative to the source of laser energy. Alternatively, the capillary 128 and optical fiber 126 may be stationary with the source of laser energy being rotated.

In a non-illustrated example, capillary tube 150 may be radially cut through a dimple free portion 148, rather than at interface 158. As such, the formed capillary 128 may include dimple free portion 148 at a proximal end, as well as a second dimple free portion at a distal end. In one aspect, capillary tube 150 may be approximately 1 meter, and may be dimpled and cut into a plurality of even or uneven capillaries 128.

The fused capillary 128 and optical fiber 126 may be implemented in laser delivery device 10 as discussed above with respect to capillary 28 and optical fiber 26 in laser delivery device 10 such that dimples 142 on dimpled portion 146 scatter the higher order mode and overfilled portions of laser energy 124. Similarly, capillary 128 with dimpled portion 146 around optical fiber 126 increases the likelihood that laser energy 124 will be internally reflected within optical fiber 126 until the energy reaches the targeted material, as shown in FIGS. 3 and 5. Dimple free portion 148 assists a user or assembler in viewing the optical fiber 126 within capillary 128 during positioning before fusing the elements together. Further, dimple free portion 148 in capillary 128 facilitates fusing of capillary 128 to optical fiber 126 by reducing interference of the laser energy by dimples 142 during the fusion process. Moreover, the method of forming a plurality of capillaries 128 from long capillary tube 150 illustrated in FIGS. 6 and 7 provides a quicker, less expensive, and more efficient procedure to form capillaries 128.

While principles of the present disclosure are described herein with reference to illustrative examples for particular applications, it should be understood that the disclosure is not limited thereto. Those having ordinary skill in the art and access to the teachings provided herein will recognize additional modifications, applications, embodiments, and substitution of equivalents all fall within the scope of the features described herein. Accordingly, the claimed features are not to be considered as limited by the foregoing description.

We claim:

1. A laser delivery device, comprising:
   a connector portion at a proximal end of the laser delivery device; and
   an optical fiber connecting the connector portion to a distal end of the laser delivery device;

the connector portion including a capillary at least partially surrounding a proximal portion of the optical fiber, wherein the capillary includes a plurality of circular dimples on at least a portion of an outer circumferential surface thereof.

2. The laser delivery device of claim 1, wherein the dimples are arranged in a pattern.

3. The laser delivery device of claim 1, wherein the dimples are arranged randomly.

4. The laser delivery device of claim 1, wherein the capillary is glass.

5. The laser delivery device of claim 1, wherein the dimples are a constant depth.

6. The laser delivery device of claim 1, wherein the dimples are varying depths.

7. The laser delivery device of claim 1, wherein the dimples are formed by melting with a $CO_2$ laser or with a green light laser, or by etching.

8. The laser delivery device of claim 1, wherein the dimples are not included on a distal outer circumferential surface portion of the capillary.

9. The laser delivery device of claim 1, wherein an outer circumferential surface of the capillary also includes projections.

10. The laser delivery device of claim 1, wherein the optical fiber includes a core surrounded by at least one cladding layer or one buffer layer;
wherein a portion of the capillary is surrounded by a crimp; and
wherein the optical fiber is at least partially surrounded by a jacket layer distal to the crimp.

11. The laser delivery device of claim 1, wherein the capillary includes a proximal end configured to be coupled to a laser source and a dimple free portion at the proximal end of the capillary;
wherein the capillary is fused to the optical fiber at proximal ends of the capillary and the optical fiber such that the fused portion of the capillary at least partially overlaps with the dimple free portion at the proximal end of the capillary; and
wherein at least a portion of the capillary is radially surrounded by a stainless steel ferrule.

12. The laser delivery device of claim 1, wherein the laser delivery device is coupled to a holmium laser.

13. The laser delivery device of claim 1, wherein the dimples extend between 1 and 50 micrometers through the radial thickness of the capillary from the outer circumferential surface of the capillary,
wherein a proximal portion of the capillary is free of dimples such that between 10 and 30 percent of the capillary is free of dimples, and
wherein at least a portion of the dimple free portion of the proximal portion of the capillary is fused to the optical fiber.

14. A laser delivery device, including:
a SubMiniature version A (SMA) connector;
the SMA connector including a capillary at least partially surrounding a portion of an optical fiber,
wherein the capillary includes dimples on at least a portion of a circumferential surface thereof, wherein the capillary includes a proximal portion configured to be coupled to a laser source, and wherein the capillary includes a dimple free portion at the proximal portion.

15. The laser delivery device of claim 14, wherein the optical fiber is fused to the capillary at least over a portion of the optical fiber that overlaps with the dimple free portion of the capillary.

16. The laser delivery device of claim 14, wherein the dimples are included on an outer circumferential surface of the capillary.

17. A laser delivery device, comprising:
a connector portion at a proximal end of the laser delivery device configured to be coupled to a laser source; and
an optical fiber connecting the connector portion to a distal end of the laser delivery device;
the connector portion including a capillary at least partially surrounding a proximal portion of the optical fiber,
wherein the capillary includes a dimple free portion at a proximal most end and a dimpled portion, and
wherein the capillary is fused to the optical fiber over an overlap of the dimple free portion of the capillary and the optical fiber.

18. The laser delivery device of claim 17, wherein the dimpled portion includes dimples on an outer circumferential surface of the capillary.

19. The laser delivery device of claim 18, wherein the dimples on the dimpled portion of the outer circumferential surface of the capillary are formed by melting with a $CO_2$ laser.

20. The laser delivery device of claim 19, wherein the dimples are circular indentations on a circumferential exterior of the capillary and extend between 1 and 50 micrometers through the radial thickness of the capillary from the outer circumferential surface of the capillary, and
wherein a proximal portion of the capillary is free of dimples such that between 10 and 30 percent of the capillary is free of dimples, and
wherein at least a portion of the dimple free portion of the capillary is fused to the optical fiber.

* * * * *